United States Patent [19]

Gergely et al.

[11] Patent Number: 5,527,540
[45] Date of Patent: Jun. 18, 1996

[54] EFFERVESCENT SYSTEM HAVING AN ALKALI-SENSITIVE AND/OR METAL-SENSITIVE, PHARMACEUTICAL ACTIVE SUBSTANCE, AND PROCESS FOR ITS PREPARATION

[75] Inventors: Gerhard Gergely, Gartengasse 8, A-1053 Vienna; Thomas Gergely, Vienna; Irmgard Gergely, Vienna, all of Austria

[73] Assignee: Gerhard Gergely, Austria

[21] Appl. No.: 228,211

[22] Filed: Apr. 15, 1994

[30] Foreign Application Priority Data

Apr. 15, 1993 [CH] Switzerland .................. 1137/93

[51] Int. Cl.⁶ .................. A61K 9/46; A61K 9/16
[52] U.S. Cl. .................. 424/466; 424/465; 424/492; 424/493; 424/496; 424/497; 514/772.3; 514/774; 514/782; 514/777
[58] Field of Search .................. 424/466, 496, 424/497, 493, 490

[56] References Cited

U.S. PATENT DOCUMENTS

4,762,702  8/1988  Gergely et al. .................. 424/44
5,306,506  4/1994  Zema et al. .................. 424/466

FOREIGN PATENT DOCUMENTS

0181564   5/1986  European Pat. Off. .
93/00886  1/1993  WIPO .

*Primary Examiner*—Thurman K. Page
*Assistant Examiner*—James M. Spear
*Attorney, Agent, or Firm*—Ostrolenk, Faber, Gerb & Soffen

[57] ABSTRACT

In the pharmaceutical formulation of at least one alkali-sensitive active substance with an effervescent system, the carbonate component is embedded in at least one edible, organic acid and is preferably covered by said acid or by another acid. The active substance is embedded in at least one of the following compounds: an edible, organic acid, a higher alcohol, a hydrocolloid or a relatively long-chain polyvinylpyrrolidone, preferably covered with at least one of the stated compounds. The contact zone between active substance and effervescent system should have a pH of not more than 4.5. Both effervescent system particles and active substance particles, which are embedded or optionally covered in this manner, may be applied to carrier crystals of the same or another acid. The mixture is preferably pressed to give tablets. The acid provided for the embedding or covering may contain 0.1 to 3 mg of ethylenediaminetetraacetic acid per tablet.

14 Claims, No Drawings

EFFERVESCENT SYSTEM HAVING AN ALKALI-SENSITIVE AND/OR METAL-SENSITIVE, PHARMACEUTICAL ACTIVE SUBSTANCE, AND PROCESS FOR ITS PREPARATION

The invention relates to a pharmaceutical formulation in the form of a mixture of at least one active substance—selected from the group consisting of alkali-sensitive and metal-sensitive active substances—with an effervescent system comprising at least one alkali metal or alkaline earth metal carbonate or bicarbonate and at least one solid, edible, organic acid; the invention relates further to a process for the preparation of such formulation.

With the current tendency to incorporate more and more new active substances into effervescent granules, instabilities are increasingly occurring in effervescent granules when particularly sensitive active substances are processed. With regard to effervescent compositions generally, such active substances can be divided into two groups: active substances which are extremely alkali-sensitive and active substances which are extremely acid-sensitive. There is frequently also high sensitivity to metal ions, which may lead to the onset of a certain amount of decomposition or degradation even when a wire sieve is used. Examples of alkali-sensitive active substances are acetylsalicylic acid, pethidine, chloramphenicol, phenobarbital, nicotinamide, benzylpenicillin and the ACE inhibitors enalapril, perindopril tertiary butylamine and ramipril; examples of sensitivity to alkalis and to heavy metal ions are morphine, acetylcysteine, ascorbic acid, thiamine (vitamin $B_1$), riboflavin (vitamin $B_2$), pyridoxine (vitamin $B_6$) and cyanocobalamin (vitamin $B_{12}$).

If, in the case of these sensitive active substances, a procedure is adopted in which the active substance is added to a prepared effervescent mixture—optionally with additional fillers—in order to minimize the contact with the effervescent mixture, it is frequently found that degradation of the active substance nevertheless occurs. In such systems, the vitamins of the B group, such as riboflavin, pyridoxine and thiamine, also exhibit degradation of up to 2%, and degradation of up to 5% after 6 to 12 months. If, for example, the active substance captopril, which is very alkali-sensitive and metal-sensitive, is added to a standard effervescent mixture in accordance with this state of knowledge, about 6% degradation of the captopril as a result of dimerization is found after only two months. Even on sieving through a conventional wire sieve, dimerizations of 0.2% or more may occur. On the other hand, the effervescent granules also still have sufficient free alkalis which come into contact with the captopril. Anchoring of this active substance on an acid crystal with the aid of a binder also does not provide sufficient protection: after 2 months, there is still degradation of about 4%. Embedding the active substance in a neutral filler also fails to solve the problem:

TABLE 1

| Degradation after 2 months: | |
| --- | --- |
| Captopril/effervescent base | 6.06% |
| Captopril-tartaric acid phase/effervescent base | 3.88% |
| Captopril-mannitol phase/effervescent base | 3.18% |

Furthermore, attempts have been made on the one hand to counteract the metal sensitivity of captopril by treatment of the effervescent mixture with a solution of ethylenediamine tetraacetic acid (EDTA) and, on the other hand, also to treat the active substance phase itself with EDTA. With heavy metals, EDTA forms complexes in which the metal can no longer have a harmful effect. These measures and combinations do result in an improvement in the degradation behavior but not yet to a satisfactory extent:

TABLE 2

| Degradation after 2 months at room temperature: | |
| --- | --- |
| Captopril + tartaric acid + EDTA/effervescent base | 2.88% |
| Captopril + tartaric acid/effervescent base + EDTA | 1.45% |
| Captopril + tartaric acid + EDTA/effervescent base + EDTA | 0.80% |

Since these procedures alone did not achieve the object, it was necessary to find structures which sufficiently protect the active substance from alkalis. Surprisingly, the problem described was solved by the measures described hereinafter. They apply to all pharmaceutical active substances which are extremely alkali-sensitive and also to those which are alkali-sensitive and metal—sensitive. Advantageous extensions of the invention are described in the examples.

The solution of the problem is based on the measure that the active substance is covered with or embedded in at least one of the compounds selected from the group consisting of solid, edible, organic acids, higher alcohols, hydrocolloids and a long-chain polyvinylpyrrolidone. The achievement of the object of the invention is further improved if an effervescent mixture is produced, for example, in such a way that the alkali metal or alkaline earth metal carbonates or bicarbonates are applied to a carrier comprising crystalline, organic acid with powdered citric acid or as a mixture with powdered acid, whereupon this layer is covered with the aid of a further powdered, edible organic acid, by means of an acid solution as binder, so that the contact zone between active substance and effervescent granules or the surface of the particles of the effervescent system has a pH of not more than 4.5. This can be determined by rolling individual granules on a moistened pH paper, after which the pH is determined from the colour development.

The object can also be achieved by granulating the carbonates and/or the bicarbonates together with powdered citric acid so that they are embedded, and covering these granules prepared in this manner, by means of an acid solution, also with a layer of a powdered, edible, organic acid.

Depending on the quality of the embedding, it may also be possible to dispense with the additional covering. If vitamins of the B group, e.g. pyridoxine, are mixed with effervescent granules prepared by this method, and the mixture is pressed to give tablets, improved stability and degradation reduced to about half are found during storage.

On the other hand, it is found, for example, that, with one and the same captopril phase, the product has substantially improved stability only when the surface of the effervescent base granules was covered with an acid layer.

While an effervescent base according to Example 2, comprising 50% of citric acid carrier, 30% of sodium carbonate-EDTA/citric acid solution and only 7% coverage with citric acid powder exhibits a degradation of as much as 0.70% after 3 months, an effervescent base of the same composition having a citric acid coverage of 20% exhibits a degradation of only 0.18% after 3 months at room temperature.

This is achieved by allowing citric acid carrier crystals to undergo a partial reaction (preferably in vacuo) with the required amount of alkali metal bicarbonate and powdered organic acid, by the addition of water, ethanol or a mixture of the two, drying the product and then wetting it with citric acid solution (ethanolic or aqueous, or mixture) and covering it with powdered citric acid, fumaric acid, adipic acid or malic acid so that it is enclosed all round. The solutions required for this purpose may already contain EDTA, or EDTA may be applied in separate solutions.

Although an active substance phase having a sufficient content of EDTA in the covering—for example 0.05 to 0.5 part by weight when applied in aqueous solution or suspension or up to 2 parts by weight when the dry powder is applied, based on 100 parts by weight of the total active substance phase, in particular 0.4 to 2 parts by weight per 100 parts by weight of active substance—already exhibits good stability in a mixture with effervescent granules covered according to the invention, a content of EDTA in the covering of the effervescent granules has in fact also proven expedient in many cases, i.e. 0.01 to 0.5 part by weight when applied in aqueous solution or suspension or 0.1 to 2 parts by weight when the dried powder is applied, based on 100 parts by weight of the effervescent granules. However, application in aqueous solution is preferred. The total amount of EDTA in an effervescent tablet is in particular in the range from 0.1 to 3 mg per tablet.

For the preparation of the effervescent granules, there are—as already mentioned above—two methods for embedding the alkalis:

EXAMPLE 1

3000 parts of a crystalline citric acid, 1000 parts of powdered citric acid, 2000 parts of sodium bicarbonate and 300 parts of sodium carbonate are granulated with ethanol so that the alkalis are embedded on the crystalline citric acid and in the powdered citric acid; the product is then dried, either at 70° C. or under a vacuum of 15 mbar at 60° C. The resulting granules are then wet with a solution of 400 parts of citric acid and 1 to 5 parts of EDTA in 200 ml of 1:1 water/ethanol, covered with 1000 parts of powdered citric acid and then dried.

EXAMPLE 2

If powdered citric acid is used for embedding alkalis or alkaline earths, the following procedure may be adopted: 4000 parts of powdered citric acid and 1700 parts of powdered sodium bicarbonate and 500 parts of sodium carbonate are treated with a solution of 200 g of citric acid in 130 ml of ethanol so that two 80 ml portions of this solution are applied; drying is carried out inbetween.

Before the second solution is dried, an EDTA solution is again applied and then covered with 1000 parts of citric acid powder. The granules are then dried at temperatures of 80° C. or in a vacuum under 10 mbar.

EXAMPLE 3

It is also possible to use tartaric acid as the carrier; the granules are then prepared entirely according to Example 1.

EXAMPLE 4

It is also possible to use 500 parts of fumaric acid for covering; the granules are then prepared entirely according to Example 2.

EXAMPLE 5

The procedure according to Example 2 is followed, except that, instead of sodium bicarbonate and sodium carbonate, calcium carbonate is embedded in the acid.

The second step required then consists in applying the alkali-sensitive active substance itself to an organic acid and anchoring it there, or embedding it in an acid. Starting from these basic principles, it is found that it is not sufficient to anchor the active substance to the citric acid; instead, the active substance must additionally be covered with an acid and/or with a hydrocolloid and/or with a higher alcohol, such as, for example, mannitol or sorbitol, so that it is protected from the effect of alkalis. Compounds such as maltodextrin, guar gum, gelatine or gum arabic are suitable for this purpose. Here too, EDTA is advantageously added in the case of the solutions required for this purpose. When different active substance phases were combined with the same effervescent base, the corresponding differences with regard to stability were found:

TABLE 3

| Degradation after 3 months at room temperature: | |
|---|---|
| Effervescent base according to Example 2 - captopril phase A1 | 0.54 |
| Effervescent base according to Example 2 - captopril phase A2 | 0.78 |
| Effervescent base according to Example 2 - captopril phase A10 | 0.28 |
| Effervescent base according to Example 2 - captopril phase A12 | 0.28 |

Explanation of the active substance phases:

A1: Captopril is anchored to the surface of tartaric acid with a PVP solution in which EDTA is dissolved.

A2: Captopril is anchored on citric acid with a PVP solution in which EDTA is dissolved.

A10: Captopril is anchored on the tartaric acid with an aqueous EDTA solution and then covered with maltodextrin and fumaric acid.

A12: Captopril is anchored on the tartaric acid with an aqueous vitamin C and EDTA solution and then covered with fumaric acid and maltodextrin.

Both the tartaric acid surface and—only slightly but nevertheless—the captopril surface are in fact partially dissolved so that they become tacky and the maltodextrin and the fumaric acid remain adhering thereon.

An improvement in stability can also be achieved with vitamin C or tocopheryl acetate as free radical acceptors in the active substance phase. It is found that optimal embedding of the active substance in the acid phase also plays a significant role with regard to the stability.

The following Examples illustrate the principle of optimal protection of the active substance by embedding:

EXAMPLE 6

25 parts of captopril are mixed with 90 parts of milled vitamin C and granulated with the aid of a solution of 10 parts of citric acid and 0.2 part of EDTA in 2 parts of alcohol and 4 parts of water. Thereafter, 25 parts of maltodextrin and 10 parts of fumaric acid are applied and drying is carried out at 60° C.—preferably by means of a vacuum.

EXAMPLE 7

25 parts of captopril are mixed with 100 parts of tartaric acid and wet with a solution of 10 parts of maltodextrin in 5 parts of water and 0.2 part of EDTA. Thereafter, the product is covered with 50 parts of mannitol and 20 parts of fumaric acid and is dried.

EXAMPLE 8

25 parts of captopril are mixed with 100 parts of citric acid powder and wet with a solution of 0.2 part of EDTA and 1 part of water; thereafter, granulation is carried out with a solution of 1 part of PVP in 3 parts of ethanol and the product is covered with 10 parts of powdered vitamin C.

EXAMPLE 9

10 parts of riboflavin are mixed with 5 parts of powdered malic acid, granulated with 1 part of PVP in ethanol solution and then covered with 10 parts of powdered sorbitol and 10 parts of citric acid.

10 parts of pyridoxine hydrochloride are mixed with 80 parts of citric acid and granulated with a solution of 1 part of ascorbic acid and 0.2 part of EDTA in 3 parts of water; the granules are then covered with 10 parts of powdered citric acid.

Combinations of these active substance phases with the effervescent bases mentioned exhibit degradation of only 0.03–0.2% after storage for 2 months at room temperature.

The invention is not restricted to the Examples mentioned. It does of course apply to all alkali-sensitive and/or metal-sensitive active substances; other edible, organic acids may also be used.

We claim:

1. A pharmaceutical formulation in the form of a particulate mixture of at least one active substance—selected from the group consisting of alkali-sensitive and metal-sensitive active substances—with an effervescent system comprising at least one alkali metal or alkaline earth metal carbonate or bicarbonate and at least one solid, edible, organic acid, wherein the active substance is covered with or embedded in at least one of the compound selected from the group consisting of solid, edible, organic acids selected from the group consisting of citric acid, tartaric acid, malic acid, ascorbic acid and adipic acid, higher alcohols selected from the group consisting of mannitol, sorbitol and xylitol, hydrocolloids and a polyvinyl-pyrrolidone.

2. A formulation according to claim 1, wherein particles of said active substance are also anchored to carrier crystals of said at least one compound.

3. A formulation according to claim 1, wherein said effervescent system is granulated and the resulting granules are covered with or embedded in said compound.

4. A process for the preparation of a pharmaceutical formulation in the form of a particulate mixture of at least one active substance—selected from the group consisting of alkali-sensitive and metal-sensitive active substances—with an effervescent system comprising at least one alkali metal or alkaline earth metal carbonate or bicarbonate and at least one solid, edible, organic acid, wherein an effervescent phase and an active substance phase are prepared separately from one another and then mixed, each phase being formed by embedding particles of carbonate or bicarbonate and active substance, respectively, in or covering them with at least one compound selected from the group consisting of solid, edible, organic acids selected from the group consisting of citric acid, tartaric acid, malic acid, ascorbic acid and adipic acid, higher alcohols selected from the group consisting of mannitol, sorbitol and xylitol, hydrocolloids and a solution of polyvinylpyrrolidone.

5. A process according to claim 4, wherein the hydrocolloid is selected from the group consisting of maltodextrin, guar gum, gelatine and gum arabic.

6. A formulation according to claim 1 wherein the hydrocolloid is selected from the group consisting of maltodextrin, guar gum, gelatine and gum arabic.

7. A formulation as claimed in claim 1, wherein said acid provided for the embedding or covering contains ethylenediaminetetraacetic acid in an amount of 0.01 to 2 parts by weight for covering 100 parts by weight of effervescent granules or 0.05 to 2 parts by weight for covering 100 parts by weight of active substance.

8. A formulation as claimed in claim 1, wherein the active substance is an ACE inhibitor.

9. A formulation as claimed in claim 8, wherein the ACE inhibitor is captopril.

10. A formulation according to claim 1, wherein the outer layer of the effervescent system has a pH of not more than 4.5.

11. A process according to claim 4, wherein said effervescent system is granulated and the resulting granules are covered with or embedded in said compound.

12. A process according to claim 4, wherein the active substance particles are applied to carrier crystals of said one compound.

13. A process according to claim 4, wherein the formulation is pressed to give tablets.

14. A process according to claim 4, wherein about 1 to about 5 mg of ethylenediaminetetraacetic acid per amount of tablet are incorporated into said compound.

* * * * *